US009114185B2

(12) United States Patent
Affaitati

(10) Patent No.: US 9,114,185 B2
(45) Date of Patent: Aug. 25, 2015

(54) APPARATUS FOR SANITIZING MEDICAL DEVICES

(75) Inventor: Pietro Affaitati, Albano Laziale (IT)

(73) Assignee: CANTEL MEDICAL SRL, Pomezia (RM) (IT)

( * ) Notice: Subject to any disclaimer, the term of this patent is extended or adjusted under 35 U.S.C. 154(b) by 0 days.

(21) Appl. No.: 14/239,741

(22) PCT Filed: Aug. 31, 2012

(86) PCT No.: PCT/IB2012/001694
§ 371 (c)(1),
(2), (4) Date: Feb. 24, 2014

(87) PCT Pub. No.: WO2013/030662
PCT Pub. Date: Mar. 7, 2013

(65) Prior Publication Data
US 2014/0205513 A1     Jul. 24, 2014

(30) Foreign Application Priority Data
Aug. 31, 2011  (IT) .............................. VI2011A0237

(51) Int. Cl.
*A61L 2/00*     (2006.01)
*B08B 3/00*     (2006.01)
*A61B 1/00*     (2006.01)
*A61L 2/18*     (2006.01)
*A61B 19/00*    (2006.01)

(52) U.S. Cl.
CPC . *A61L 2/18* (2013.01); *A61B 19/34* (2013.01); *A61B 2019/343* (2013.01); *A61L 2202/24* (2013.01)

(58) Field of Classification Search
CPC ................ A61L 2/00; A61L 2/18; A61L 2/26
USPC ......... 422/28, 292, 300; 134/56 R, 94.1, 201; 600/133
See application file for complete search history.

(56) References Cited

U.S. PATENT DOCUMENTS 6,656,423 B1 * 12/2003  Joslyn ............................... 422/1
2008/0115814 A1  5/2008  Hasegawa
2009/0048133 A1  2/2009  Kanno

FOREIGN PATENT DOCUMENTS

| EP | 1767140 | 3/2007 |
| WO | 0156615 | 8/2001 |
| WO | 03084578 | 10/2003 |
| WO | 2004043499 | 5/2004 |

* cited by examiner

Primary Examiner — Monzer R Chorbaji
(74) Attorney, Agent, or Firm — Themis Law

(57) ABSTRACT

A machine for cold sanification of medical devices includes a sanification chamber adapted to house at least one medical device to be treated, a first delivery system supplying one or more sanification fluids and having a plurality of hydraulic circuits each having a drawing conduit for the sanification fluids connectable to a respective reservoir and a plurality of delivering conduits connected with the sanification chamber for introducing the pressurized fluids therein, a second delivery system fluidically connecting one or more of the drawing conduits with corresponding inner channels of a device housed into the sanification chamber. The first delivery system includes a central collector interposed between the drawing conduits and the delivering conduits, which receive from the first the fluids and supply to each of the delivering conduits the sanification fluids at substantially the same pressure.

13 Claims, 5 Drawing Sheets

ABSTRACT

APPARATUS FOR SANITIZING MEDICAL DEVICES

TECHNICAL FIELD

The present invention is generally applicable to the field of devices for sanification, disinfection, decontamination and sterilization treatments of reusable medical devices and has particularly as an object a machine for the sanification of medical devices after use on a patient.

STATE OF THE ART

As is known, all medical devices designed to come into contact with the body of a patient during treatment and diagnosis require, before being re-used on a new patient, to be "reprocessed", i.e. to be subjected to a treatment of more or less advanced sanification.

Such sanification treatment may be a simple disinfection treatment or a sterilization process, performed both at hot and cold temperature, also depending on the materials the various devices are made.

For example, medical devices which are sensitive to the relatively high temperatures of disinfection autoclaves are used to be cold treated by a washing liquid, generally water, comprising in solution one or more chemical agents having more or less high decontaminating/sterilant properties.

Typically, the machines for the sanification treatment of medical devices comprise a compartment for housing one or more reservoirs of corresponding cleaning and/or decontaminating liquids.

These liquids are drawn by respective pumping devices and transferred by means of corresponding hydraulic circuits inside a sanification chamber in which the medical device to be treated is housed.

In particular, the liquids are introduced into the chamber through a plurality of delivery conduits.

If a device has to be treated which comprises an outer sheath that encloses a plurality of channels, such as a flexible endoscope, it is necessary to connect a part of the delivery conduits to the inner channels of the device, so as to allow the passage of liquids even at their inside.

WO2005056060 discloses a machine for the sanification of endoscopes provided with a removable container defining the sanification chamber and designed to house an endoscope. The connection of the inner channels to the delivery conduits of the liquids is obtained by means of suitable connections arranged both at the container wall and inside of a housing compartment of this latter provided in the machine frame. Each connection is adapted to connect the respective channel to be served to the supplying reservoirs via a respective hydraulic circuit separated from the others and provided with a respective pumping device. Consequently, each circuit also needs its own control devices, in particular solenoid valves for the selective opening/closing of the respective circuits. However, this configuration appears to be excessively complex and obviously the high number of components causes an increased risk of breakage and consequent machine downtime.

Furthermore, this configuration does not allow to maintain uniform the flows supplied to each channel because each circuit is adjusted independently from the others. Consequently, there is a risk that one or more of the channels of the device receives a flow not sufficient to ensure proper sanification, while others could be overcharged.

Another machine for sanification of endoscopes is disclosed in WO03/084578, wherein the endoscope is inserted into a shell defining a watertight sanification chamber thereinside provided with inlet and outlet openings of the sanification liquids fed by pumping means connected to a single supply channel.

However, the inner channels of the endoscope do not have a direct connection with the supply channel and the inflow of the sanification liquid thereinside is only due to the delivery pressure of the liquid within the chamber. Consequently, the machine does not guarantee adequate circulation of the sanification liquid inside the inner channels of the endoscope and their effective sterilization.

WO2004/043499 discloses a machine for reprocessing endoscopes wherein the inner channels of the endoscope are individually connected with respective delivery conduits of the supply circuit through respective connection pipes. These latter are connected to one or more reservoirs for feeding one or more sanification liquids, possibly with the interposition of a reaction chamber of the reagents contained in the respective reservoirs. The flowing of the liquid within the sanification circuit, and then towards the inlet conduit, is realized by a pump located upstream the reservoirs. Therefore, no control of pressure on the single delivery conduits is provided, with the consequent drawback that one or more channels of the device could receive a flow not sufficient to ensure its proper sanification.

A similar machine is disclosed in WO01/56615, wherein the flowing of the liquid within the single delivery conduits, adapted to be directly connected with the respective channels of the endoscope, is entrusted to a single pump.

EP1767140 discloses a machine for disinfection of endoscopes wherein the inner channels of the endoscope are connected to respective delivery conduits via a multiple connector. Even in this case, however, there is no device adapted to receive the sanitizing liquid and distribute it in a controlled manner to the single channels so as to ensure that in each of them the liquid flows with the right pressure.

DISCLOSURE OF THE INVENTION

An object of the present invention is to overcome the above mentioned drawbacks, providing a machine for cold sanification of medical device which has properties of high efficiency and relative cost-effectiveness.

A particular object is to provide a machine for the cold sanification of medical devices provided with inner channels which allows to control in a precise manner the flow of sanification fluids within each channel.

Yet another object of the present invention is to provide a machine for the cold sanification of medical devices that allows to uniformly deliver the sanification fluids inside the channels of the device to be treated.

These objects, and others which will become more apparent hereinafter, are achieved by a machine for cold sanification of medical devices, as described hereinafter.

Thanks to this particular combination of features, all the inner channels of the medical device will be fed with a fluid or fluids mixture having the same pressure, thus allowing a unique and precise adjustment of the flow.

Moreover, it will not be necessary to provide a large number of regulators and pumping devices, increasing the simplicity of construction and the operability of the machine and therefore also its reliability.

Advantageous embodiments of the invention are obtained according to the dependent claims.

BRIEF DISCLOSURE OF THE DRAWINGS

Further characteristics and advantages of the invention will become more apparent in light of the detailed description of preferred but not exclusive embodiments of a machine according to the invention, shown only by way of non-limiting example with the aid of the accompanying drawings in which.

BEST MODE OF CARRYING OUT THE INVENTION

With reference to the above figures, there is shown a machine for cold sanification of reusable medical devices, such as rigid or flexible endoscopes, optical devices or other tools and equipment for diagnostic and/or surgical use, of the type having a sheath enveloping one or more inner channels.

A machine according to the invention, generally indicated with 1, may be used to perform a more or less advanced sanification treatment, or "reprocessing" of the devices, which may be treatments of simple cleansing or of disinfection and/or sterilization, preferably cold treatments, or through working fluids already active at temperatures substantially close to the environment temperature.

More precisely, the level of disinfection or sterilization of the device may be linked to the disinfectant/sterilizing properties of the chemical agents in solution or dispersed in a liquid carrier, generally water, and/or to the contact and immersion time of the devices in the liquid.

Figure 1:
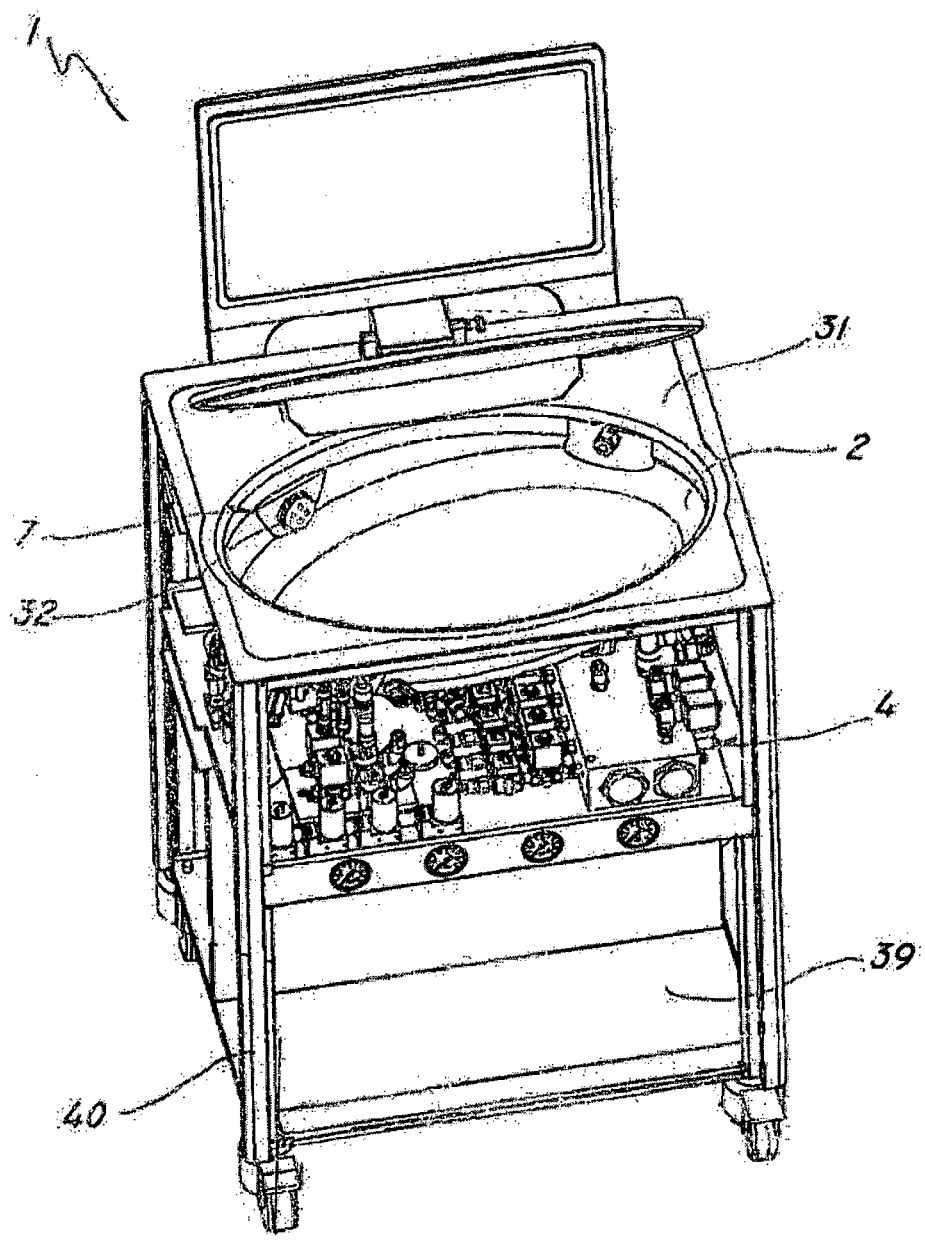
FIG. 1 is an elevational view of a machine of the invention in a first preferred embodiment.
Figure 3:
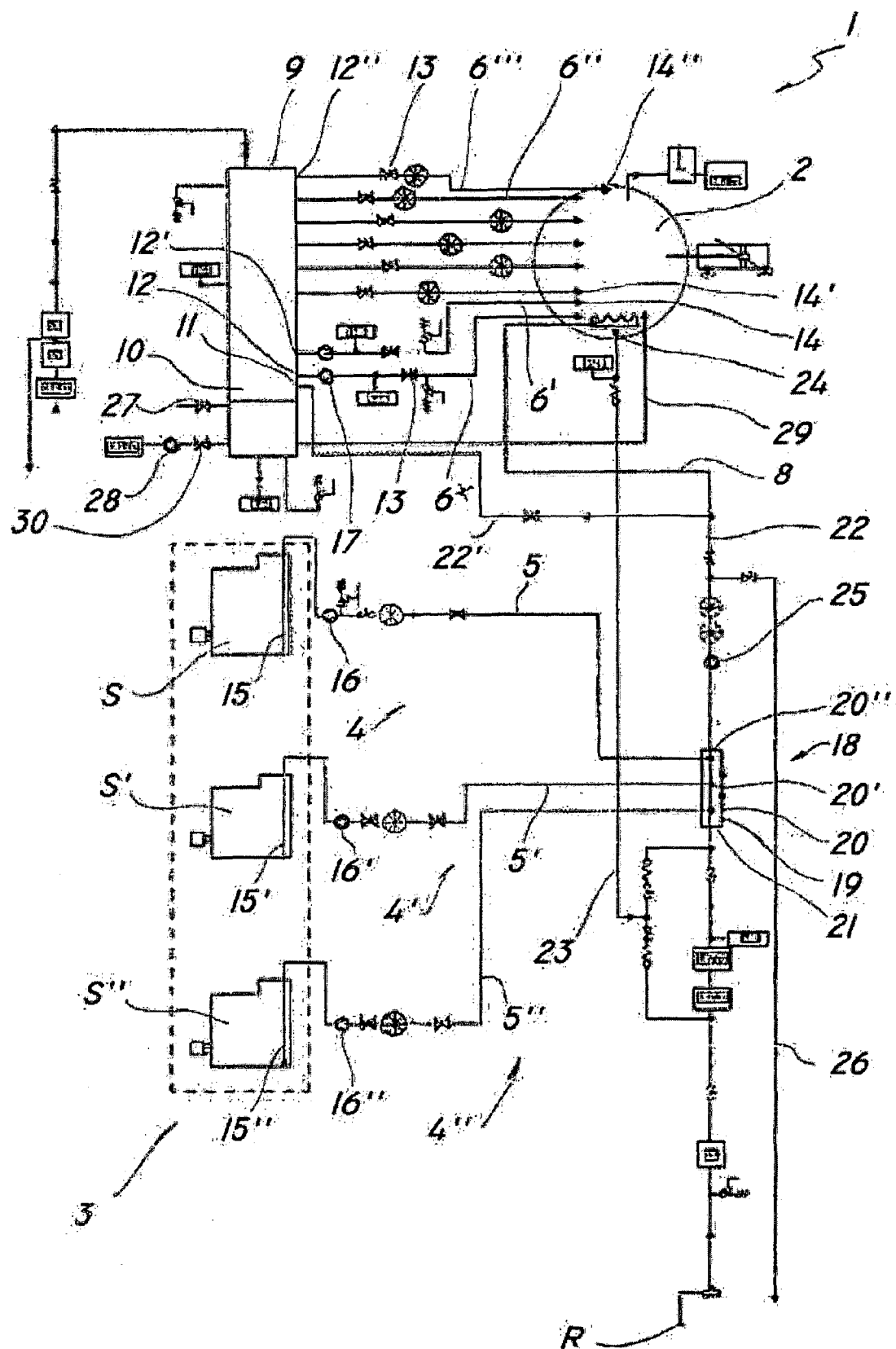
FIG. 3 represents the hydraulic scheme of a machine of the invention in the embodiment of FIG. 1.

With reference to FIGS. 1 and 3, a machine 1 according to the invention will comprise essentially at least one sanification chamber 2 housing at least one medical device to be treated, not illustrated since of per se known type, and means 3 for supplying one or more sanification fluids within the sanification chamber 2.

The supplying means 3 comprise a plurality of hydraulic circuits 4, 4', 4" each having a drawing conduit 5, 5', 5" for the sanification fluid connectable to a respective reservoir S, S', S" and a plurality of delivery conduits 6, 6', 6", . . . connected with the sanification chamber 2 to deliver the same fluids under pressure.

Means 7 are also provided for the fluidic connection of at least part of the delivery conduits 6, 6', 6", . . . to corresponding inner channels of the device each time housed in the sanification chamber 2.

A delivery pipe 8 is also provides which is designed to be connected to the inner channels of the device to supply the fluid directly into the sanification chamber 2 in order to treat the surface of the medical device.

According to a feature of the invention, the delivery means 3 comprise at least one central collector 9 interposed between the drawing conduits 5, 5', 5" and at least part of the delivery conduits 6, 6', 6", . . . for receiving from the first the sanification fluids and distributing the same to the delivery conduits 6, 6', 6", . . . with substantially the same value of pressure P and subsequently supplying the fluids to the connecting means 7.

In a preferred but purely exemplifying embodiment the supply pressure P may be between 1 and 5 bar and even more preferably between 2 and 4 bar.

In particular, the collector 9 will comprise a mixing chamber 10 for the sanification fluids having at least one inlet 11 for the drawing conduits, hereinafter referred for simplicity only with reference 5, and one outlet 12, 12', 12", . . . for each of the delivery conduits 6, 6', 6", . . . .

Hereinafter, for simplicity, and unless otherwise specified, the delivery conduits and related parts will be indicated only with a number without superscript, it being understood that everything to be said for the conduit 6 will be provided in a substantially similar manner also in the other delivery conduits 6', 6", . . . .

Preferably, the delivery conduits 6 connected to the collector 9 will be those designed to be connected to the inner channels of the medical device.

By contrast, the delivery pipe 8 designed to supply the fluid directly into the sanification chamber 2, externally to the device, may be connected to drawing conduits 5 without the interposition of the collector 9.

Suitably, the supplying means 3 comprise adjustment means 13 of the flow rate associated to each of the delivery conduits 6 and for example defined by a plurality of solenoid valves associated with each delivery conduit 6, generally at the respective outputs 14, so as to enable/disable the same in a selective and reciprocally independent manner, as a function of the cleaning cycle to be carried out.

Each drawing conduit 5 may comprise a picking spear 15, 15', 15" designed to be inserted into a respective reservoir S, S', S", immersed in the fluid, and a first pumping device 16, 16', 16" adapted to promote the circulation of the fluid from the respective reservoir S, S', S" to the mixing chamber 10.

Suitably, the supplying means 3 may comprise one or more second pumping devices associated with one or more of the delivery conduits 6, downstream of the collector 9.

In the exemplificative but not limiting embodiment of the figures, two second pumping devices 17, 17' are provided which are associated with corresponding delivery conduits 6, 6'.

However, it may also be provided only one of supply ducts 6 associated with a second pumping device or may be provided more than two conduits, but preferably less than the total number of delivery conduits 6.

Said second pumping devices 17, 17' will be adapted to raise the supply pressure of the fluids in the corresponding delivery conduits 6, 6' with respect to the output value from the collector 9, depending on the operational needs.

Preferably, the supplying means 3 may comprise a fluid recirculation circuit 18 having a premixing chamber 19 with first inlets 20, 20', 20" connected to respective drawing conduits 5 and a second inlet 21 connected to the water net R supplying water thereinside so as to mix the sanification fluids with water drawn from the net R and obtain a sanification mixture with a predetermined concentration of the selected chemical agents.

The premixing chamber 19 will also have an outlet conduit 22 connected to the mixing chamber 10 to send to the same the mixture of sanification fluids.

Furthermore, the recirculation circuit 18 will include a recovery duct 23 connected with the sanification chamber 2 for at least partially recovering the mixture after its passage through the inner channels of the medical device, as well as the mixture supplied directly into the sanification chamber 2 from the pipe 8, and re-enter it in the premixing chamber 19.

Preferably, the input 24 of the recovery duct 23 will be realized on the wall of the sanification chamber 2 and may be associated to a solenoid valve for its selective opening/closing.

Suitably, the recirculation circuit 18 will include a third pumping device 25 associated with the outlet conduit 22 of the mixture and dimensioned to promote the flowing of the mixture towards the mixing chamber 10 and subsequently towards the sanification chamber 2.

The third pumping device 25 also promotes the inverse flowing of the mixture or water/fluid solution from the sanification chamber 2 to the premixing chamber 19 so as to determine the recirculation.

Suitably, the outlet conduit 22 of the premixing chamber 19 will have two branches, a first 22' of which will be connected to the collector 9, while the other will be connected directly to the sanification chamber 2, thus defining the delivery pipe 8.

Moreover, the outlet conduit 22 can also be connected to an exhaust pipe 26 of the liquid at the end of the cleaning cycle.

The machine 1 may also comprise means 27 for supplying compressed air inside the sheath of the medical device to test its air-tightness. The air supply pressure may be between 100 mbar and 400 mbar and preferably between 200 mbar and 250 mbar.

The compressed air supply means 27 may include a compressor 28 having a delivery pipe 29 adapted to be connected, through a respective solenoid valve 30 and the connecting means 7, within the sheath of the medical device to supply thereinto air at high pressure and to test, by means of suitable pressure sensors, its integrity.

A circuit for feeding air at a pressure of between 1 and 2 bar, for example close to 1.5 bar, may be also provided, for the final drying cycle of the device.

As shown in FIG. 3, each delivery conduit 6 may have an outlet 14 formed in the side wall of the sanification chamber 2.

Figure 2:
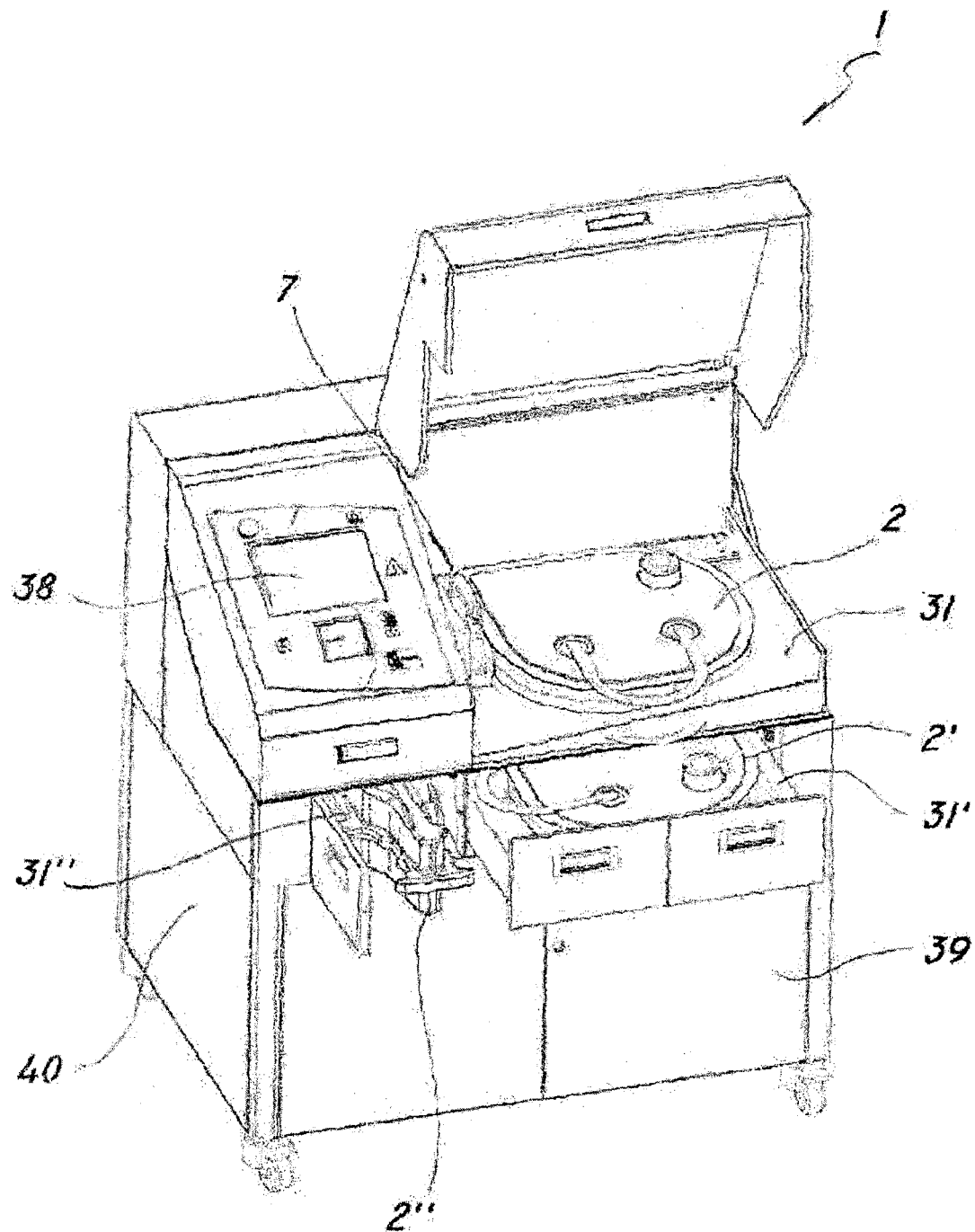
FIG. 2 is an elevational view of a machine of the invention in a second preferred embodiment.

In particular, the sanification chamber 2 can be defined by a fixed bowl, as in FIG. 1, or from a bag or case removably housed in a suitable compartment 31 of the machine 1, as in the configuration of FIG. 2.

In the latter case the case 2 will be adapted to be removed from the compartment 31 at the end of each reprocessing cycle for storing the sanitized device in a protected environment outside the machine 1, thus allowing to carry out a new cycle to be carried out on a different device without compromising the previous cycle.

Figure 6:
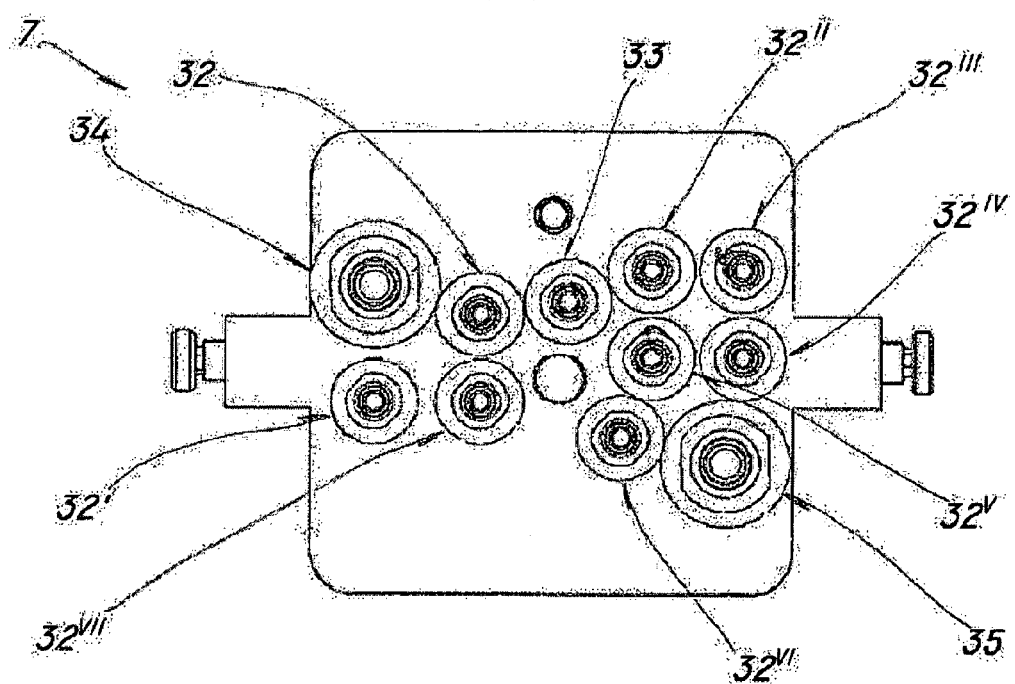
FIG. 6 is a front view of a particular of the case of FIG. 5.

In particular, it could be observed that in the embodiment shown in FIG. 6, there are eight connectors 32-32.sup.vii for the connection of a respective delivery conduit 6 to a corresponding channel of the device, a connector 33 to connect the inside of the sheath to the compressed air supply means 27, a connector 34 for connecting the pipe 8 for loading the water and a connector 35 for connecting the sanification chamber 2 to the exhaust pipe 26.

If the sanification chamber 2 is defined by the removable case, the connectors will be integral to the same and will be made connectable to the delivery conduits 6, 8 through additional connectors, not shown in the figures, arranged in the housing compartment 31 and adapted to be coupled to connectors of the case 2 in a male and female manner.

The fluidic connection means 7, for both of the embodiments, may include a plurality of pipes, not shown, adapted to removably connect each output 14 of the delivery conduits 6 to a respective inner channel of the medical device.

In particular, each connector pipe can be housed in the sanification chamber 2 and may have one end connected to a corresponding connector 32-32.sup.vii, 33 and the opposite end connectable to a corresponding channel of the device or within the sheath of the device.

The number of connectors may be even higher than the number of connecting pipes each time arranged in the sanification chamber 2 so as to allow the sanitizing treatment of medical devices having a differentiated number of channels.

The connecting pipes may be connected to the channels or within the sheath of the device by means of connecting elements, not shown, of per se known type and commonly available on the market, whose type can also vary depending on the brand of the device.

Suitably, the pipes can be connected in a removable manner both to the channels that the connectors 32-32.sup.vii, 33.

In the embodiment of FIG. 2, a machine 1 is shown which comprises a plurality of sanification chambers each adapted to be connected to the same reservoirs S, S', S" by means of respective fluid supplying means 3.

In particular, two cases 2, 2' of the removable type are provided which are housed in respective compartments 31, 31' and adapted to house both medical device of the flexible type, in particular endoscopes, and rigid devices, and a box-case 2" for the containment of rigid optical devices, which is also removably inserted in a respective compartment 31".

Figure 4:
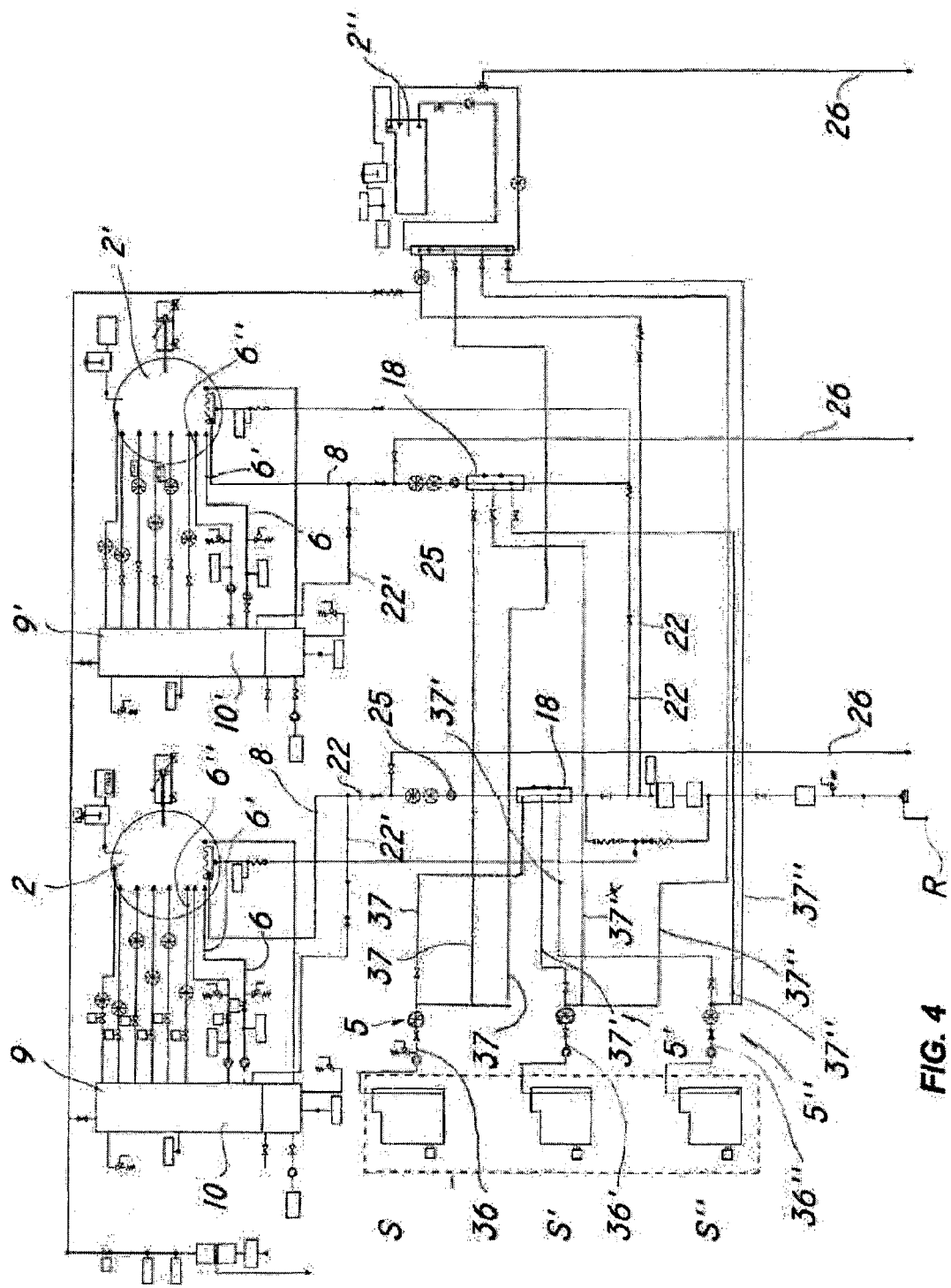
FIG. 4 represents the hydraulic scheme of a machine of the invention in the embodiment of FIG. 2.
Figure 5:
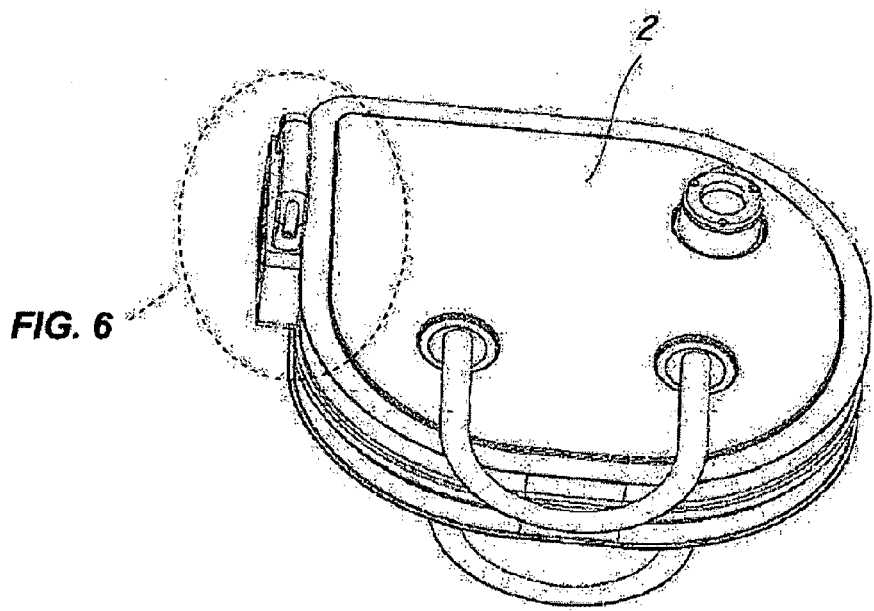
FIG. 5 is an elevational view of a case for medical devices adapted to be used with the machine of the invention.

As shown in the hydraulic diagram of FIG. 4, the supply means 3 may have a collector 9, 9' as above disclosed for each of the circuits 4, 4', 4" adapted to feed the cases 2, 2'. In particular, each of these collectors 9, 9' may have the respective drawing conduits 5, 5', 5" connectable to the reservoirs S, S', S" and respective delivery conduits 6, 6', 6", . . . connected to the respective sanification chamber 2, 2'.

The portion of the circuits 4, 4', 4" suitable to serve the box-case 2" for the rigid devices may instead be devoid of collector as such devices are not generally provided with inner channels.

Preferably, each drawing conduit 5 may comprise a single starting section 36, 36', 36" provided with a respective picking spear 15, 15', 15" and associated with a respective first pumping device 16, 16', 16".

Furthermore, the starting section 36, 36', 36" branches off into a number of end sections 37, 37', 37" equal to the number of sanification chambers 2, 2', 2" to be served to transfer fluids to each of them.

The hydraulic circuits 4, 4', 4" which will serve the different sanification chambers 2, 2', 2" may be similar to those described above with reference to the machine 1 with a single sanification chamber 2.

In both configurations, auxiliary devices may also be provided, such as pressure sensors, liquids presence sensors, level sensors, the latter associated with the sanification chamber, or temperature sensors, filtration devices, counters for the calculation of liters of the supplied fluid.

The machine 1 can be finally provided with electronic control means, for example with a graphical user interface with touch screen 38 for configuring and controlling the work cycles.

The number and type of reservoirs S, S', S" may vary in function of the cleaning cycle to be carried out and they can be housed in a special compartment 39 formed in the frame 40 of the machine 1 and will be connected to drawing conduits 5 by means of respective spears 15, 15', 15.

In the shown configuration there is a first reservoir S for a detergent and decontaminant solution containing a multi-enzymatic synergized mixture with a molecule of Adazone®, a second reservoir S' for a first sterilizing solution with a 5% solution of peracetic acid and a third reservoir S" containing a second sterilizing solution containing Adazone® and adapted to cooperate with the first to activate it. Still by way of example, the sterilizing molecule indicated above may be that described in European patent EP 1059292 or in European patent application EP 2099501, both by the same Applicant.

One of the solutions may be the one described in Italian patent application RM2005A000597 by the same Applicant.

From the above description it is evident that the invention achieves the intended objects and in particular to make available a machine for the cold sanification medical devices of relatively simple construction and which allows precise control and uniform application of supply pressure of the sanification fluids.

The invention claimed is:

1. A machine for cold sanification of medical devices, wherein each medical device has a sheath enveloping one or more inner channels to be treated with one or more sanification fluids contained in respective reservoirs, which machine comprises:

at least one sanification chamber adapted to house at least one medical device to be treated;

a first delivery system supplying one or more sanification fluids comprising a plurality of hydraulic circuits, each having a drawing conduit for the sanification fluids that is connected to a respective reservoir, and a plurality of delivering conduits having respective outlet into said sanification chamber for introducing the sanification fluids in pressurized form therein; and a second delivery system fluidically connecting one or more of said delivering conduits with corresponding inner channels of the device housed into said sanification chamber;

wherein said first delivery system comprises a plurality of pipes having one end fluidly connected with a corresponding outlet of a corresponding delivery conduit and the opposite end adapted to be removably connected to a corresponding inner channel for supplying fluid directly thereinside with a predetermined pressure;

wherein said first delivery system further comprises a central collector interposed between said drawing conduits and said delivering conduits and having thereinside a mixing chamber of the sanification fluids drawn from the reservoirs and received in said drawing conduits to be supplied to each of said delivering conduits, said mixing chamber having at least one inlet for said drawing conduits and a plurality of outlets to each of which a respective delivering conduit is joined to have, at the outlets of the delivery conduits, pressures equal with each other; and wherein said first delivery system comprises a circuit for recirculation of the fluids having a pre-mixing chamber with first fluid inlets connected to said drawing conduits.

2. The machine as claimed in claim 1, wherein said mixing chamber comprises only one inlet, said pre-mixing chamber comprising an outlet conduit adapted to connect said drawing conduits with said mixing chamber.

3. The machine as claimed in claim 2, wherein said pre-mixing chamber comprises a second inlet connectable to a water supply net for obtaining a mixture of the sanification fluids and water to be fed to said mixing chamber through said outlet conduit.

4. The machine as claimed in claim 2, wherein said circuit for recirculation comprises a recovering conduit connected with said sanification chamber to recover at least part of mixture of the sanification fluids and water after passage through the inner channels of the medical device and reintroduce it in said pre-mixing chamber.

5. The machine as claimed in claim 1, wherein said first delivery system comprises a flow-rate adjustment device associated to each of said delivering conduits, said flow-rate adjustment device comprising at least one solenoid valve applied to each of said delivering conduits for the controlled and selective closing/opening thereof.

6. The machine as claimed in claim 1, wherein said first delivery system comprises first pumping devices associated to the corresponding of said drawing conduits to promote flow from the respective reservoirs toward said collector.

7. The machine as claimed in claim 6, wherein said first delivery system comprises second pumping devices associated to one or more of said delivering conduits, downstream of said collector, and adapted to increase the pressure of the sanification fluids in the corresponding delivering conduits.

8. The machine as claimed in claim 7, wherein said circuit for recirculation comprises a third pumping device associated to said outlet conduit of the recirculated fluids.

9. The machine as claimed in claim 1, further comprising an inlet supplying compressed air within the sheath of the medical device to test air pressure tightness.

10. The machine as claimed in claim 1, wherein said outlets of said delivering conduits are formed in a lateral wall of said sanification chamber.

11. The machine as claimed in claim 1, wherein the machine comprises a plurality of sanification chambers each connectable to the reservoirs of the sanification fluids through said first delivery system of the sanification fluids.

12. The machine as claimed in claim 11, wherein said first delivery system comprises at least two collectors connectable to the reservoirs through respective drawing conduits and each connected to one of said sanification chambers by a respective plurality of delivering conduits.

13. The machine as claimed in claim 12, wherein each of said drawing conduits comprises a single starting section that is provided with a pumping device and that branches into a plurality of end sections connected to one of the sanification chambers.

* * * * *